Figure 1:
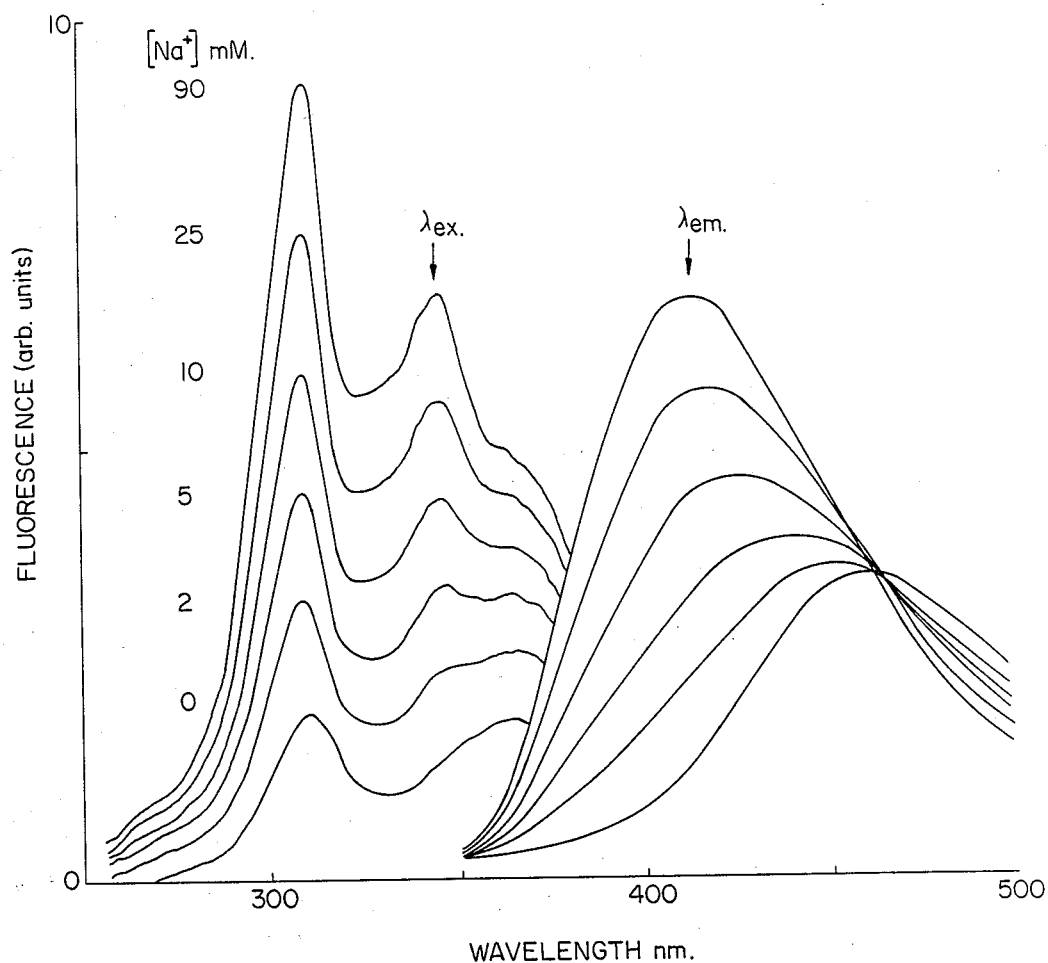

United States Patent [19]

Smith

[11] Patent Number: 4,843,158
[45] Date of Patent: Jun. 27, 1989

[54] [2,2,1]CRYPTAND COMPOUNDS THAT SELECTIVELY BIND SODIUM

[75] Inventor: Gerald A. Smith, Cambridge, Great Britain

[73] Assignee: Amersham International PLC, Little Chalfont, England

[21] Appl. No.: 932,643

[22] Filed: Nov. 19, 1986

[30] Foreign Application Priority Data

Nov. 22, 1985 [GB] United Kingdom ................ 8528804

[51] Int. Cl.⁴ .......................................... C07D 498/06
[52] U.S. Cl. .................................... 540/469; 540/468
[58] Field of Search ............................... 540/468, 469

[56] References Cited

PUBLICATIONS

Smith et al., CA106-115945m (1987).

Primary Examiner—Anton H. Sutto
Assistant Examiner—Cecilia Shen
Attorney, Agent, or Firm—Wenderoth, Lind & Ponack

[57] ABSTRACT

A compound having the property of selectively binding sodium ions in the presence of potassium ions and having the formula:

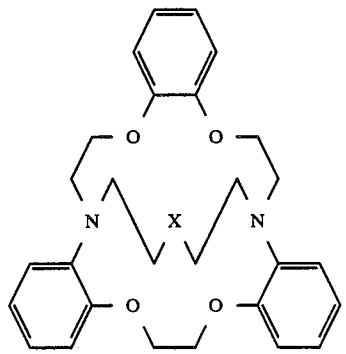

where X is

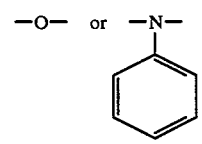

and where any aromatic ring may be substituted and/or may form part of a fused aromatic ring system.

At least one of the aromatic rings may be substituted by a spectroscopic reporter group, a group which permits the compound to enter and remain in a cell and/or an electron donating or withdrawing group.

A method of determining cytoplasmic sodium concentration by using this compound as a probe is also described.

5 Claims, 1 Drawing Sheet

[2,2,1]CRYPTAND COMPOUNDS THAT SELECTIVELY BIND SODIUM

This invention relates to compounds which have the property of selectively binding sodium ions in the presence of potassium ions. Depending on other properties which may be built into the compounds, they may be useful as probes for investigating sodium ion concentration, particularly within cells. Other uses envisaged include ion-selective electrode and transport membranes for sodium, and generally for the separation of sodium from other ions.

The importance of cytoplasmic calcium and proton activities in cellular metabolic control has been recognised for many years. Probes using fluorescent and 19-F n.m.r indicators for cytoplasmic calcium and protons, and also for magnesium, have been described in the literature. In mammalian cells, two other ions, namely sodium and potassium, contribute the major part of the osmolarity of the system. Previous studies of cellular sodium ion concentrations have mostly been effected by a sodium selective electrode, and have in consequence been limited to single robust well-anchored cells. A spectroscopic method, based on 23-Na n.m.r., has only been used with success on red blood cells.

There is a need for a spectroscopic probe for sodium ions which can be introduced into the cytoplasm of intact cells in suspension or in intact tissue.

The compounds with which the present invention is concerned are of the kind known as [2,2,1] cryptands. These are cage-type bicyclic crown compounds whose two bridgeheads consist of two —N≡ groups joined by three chains containing respectively two, two and one electron donor atoms selected from O and N. The cryptands generally are known to show good stability and high ion selectivity; but the compounds reported have limited solubility in aqueous media, and most binding constants have been reported in organic-based media. For a fuller discussion of the cryptands, reference is directed to the book "Crown Compounds, their Characteristics and Applications", by Michio Hiraoka, Elsevier, 1982.

This invention provides compounds having the property of selectively binding sodium ions in the presence of potassium ions and having the formula:

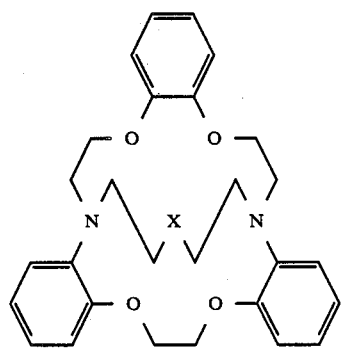

(I)

where X is

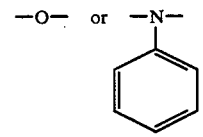

—O— or —N— and where any aromatic ring may be substituted and/or may form part of a fused aromatic ring system.

For use as a probe for the measurement of intracellular sodium ion activity, a compound needs to satisfy the following criteria:

(i) The compound must carry a spectroscopic reporter group that is sensitive to sodium binding and is useable in a biological context.

(ii) The compound must have a high selectivity for sodium over other ions, particularly hydrogen, calcium and potassium, at the sort of pH likely to be encountered in the cell (typically 7.0–7.5).

(iii) The sodium complex must have a dissociation constant of the same order as the expected sodium ion concentration in the cytoplasm (typically 5–50 millimolar).

(iv) The compound should be provided with means for entering and remaining in the cell.

(v) The compound should preferably have no adverse effect on cellular function.

Certain compounds according to this invention fulfill all five criteria and are thus useful for measuring intracellular sodium ion activity. Other compounds of the invention, which do not fulfill all the criteria, are nevertheless useful for other purposes involving selective binding of sodium ions.

Compounds where X is —O— demonstrate a selectivity for sodium ions over potassium ions of the order of $10^4$, and very tight binding of sodium ions. As a result of this tight binding, these compounds do not satisfy criterion (iii) and are not suitable as probes for intracellular sodium. They are expected to be of value for sodium-selective electrodes, however.

Compounds where X is —N(Phenyl)— demonstrate good selectivity for sodium ions over potassium ions. The sodium complexes of these compounds have dissociation constants in the region of 5–50 mM. So these compounds meet criterion (iii) and may (depending on other properties) be suitable as probes for intracellular sodium.

Depending on the nature of X, compounds of this invention may contain 3 or more aromatic rings per molecule. Any or all of these aromatic rings may carry substituents at any free position. Various kinds of substituents will now be described.

(a) In order to act as a probe, the compound needs to carry a spectroscopic reporter group or atom, the nature of whose signal depends on the presence or absence of chelated sodium. For example, for fluorescent studies, a fluorophore is required. Suitable fluorophores, and suitable methods of providing them attached to aromatic rings of the compounds of formula (1), are well known to those skilled in this field and will not be described here.

For n.m.r. studies, a fluorine atom is required and may be included in the compound, as described in the experimental section below and known to those skilled in the field.

While one reporter group or atom per molecule is sufficient, two or more may be advantageous to generate a stronger signal, provided only that they do not drastically alter the other properties of the compound. We have found that the selectivity of the compounds for sodium ions is only marginally affected by the presence of reporter groups or atoms.

(b) In order to act as a probe for intracellular sodium, the compound needs to carry one or more groups which permit the compound to enter the cell and remain in the cell. Entry involves passing through the cell membrane, for which purpose the compound needs to be in a neutral hydrophobic condition. A method has been described for introducing chelators into the cytoplasm of cells (R. Y. Tsien, Nature, Vol.290, Apr. 9, 1981 527-8). This involves providing on the compound acetoxymethyl esters of anilinodiacetic acid groups, which are hydrophobic and hence membrane permeable, and hydrolysable by cellular esterases to give membrane impermeant free acids.

To give good retention in the cytoplasm, the probe should preferably carry an excess of carboxylate negative charges over and above the number neutralised by any chelated sodium ion to prevent leakage by an ionophoric mechanism. Thus the probe synthesis should preferably incorporate at least two aromatic nitro groups for subsequent conversion to aminodiacetic acids.

(c) In order to act as a probe for intracellular sodium, the compound should not be sensitive to hydrogen ion concentration at the sort of pH likely to be encountered in the cell (typically 7-7.5). A pKa in the region of 7 would reduce the usefulness of a probe. If this problem is encountered, it is readily dealt with by adjusting the substitution pattern of the aromatic ring system. For this purpose, an electron donating or withdrawing group may be introduced into an aromatic ring. For example, an acyl, e.g. acetyl, group may be introduced by a reaction catalysed by zinc chloride. It has been found that a single acyl group, although at a distance from the grouping apparently responsible for introducing a protonation site, can reduce a pKa sufficiently for the compound to give a flat response to pH in the pH range 7-7.5.

(d) Other substituents may be present for various purposes. For example, one or more of the aromatic rings may carry a hydrocarbon substituent or may form part of a fused aromatic ring system.

The high selectivity of the cryptands for sodium is steric in origin, and the order of magnitude of the affinity is determined by the anilino substitution at X (position 21 of the cryptand). Preparation of a more fluorescent analogue should require simple extension of one of the existing chromophores with no change in the basic tribenzo-cryptand structure.

The sensitivity of F-cryptand fluorescence to sodium binding over the whole ultra violet range indicates that substitution of any one of the aromatic chromophores for a longer wavelength fluorophere would lead to an indicator with improved fluorescence. However, this is not always found in practice.

Substitution of the chromophore at position 14, 15 gives compounds which, although retaining sodium binding, show little accompanying change in long wavelength fluorescence.

As mentioned previously, the group at position 21 is central to sodium binding. It appears that retention of the amino-diacetic substituent meta to the 21 amino group is necessary to control the pK of the proposed indicator. The 21(3-amino-1-naphthyl)diacetic acid analogue of F-cryptand shows all the attributes of F-cryptand as well as good fluorescence changes at long wavelengths. However, even after further acylation the dissociation constant is too low to be useful as an indicator for sodium concentrations above 10 mM. It will be appreciated, however, that these analogues, and some of the others described hereafter, while not fulfilling all of the criteria listed above, may nevertheless find useful applications involving the selective binding of sodium atoms.

It has been found that moving the two fluorine substituents from positions para to nitrogen to those para to oxygen, results in a four fold reduction in sodium binding strength.

A particularly preferred compound of the present invention has the formula:

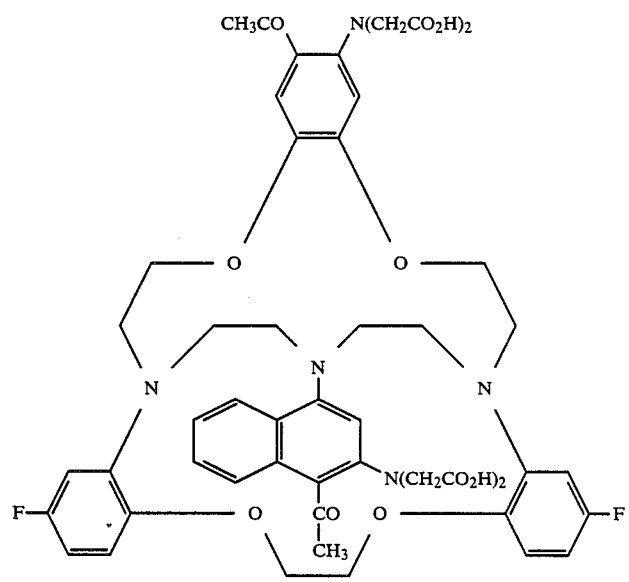

FIG. 1 shows the results of fluorescence titrations performed using a hydrolyzed probe of this compound at 20 μM in 50 mM KH$_2$PO$_4$, 100 mM KCl buffered to pH 7 with potassium hydroxide solution at 37° C. The titrations were performed on a Perkin-Elmer 44E spectrofluorimeter with bandwidths set at 4 μm. The excitation and emission spectra were obtained at the wavelengths indicated. At 10 mM sodium, no change was observed on increasing the potassium concentration to 300 mM. A pH increase of 0.1 at pH 7 gives only a small increase in fluorescence equivalent to an increase in sodium level of <3%.

The compounds may be prepared by standard chemical reactions. The following reaction scheme illustrates a typical sequence as described in the Example 1 below:

Y =
i —OEt
ii —OH

X =

-continued

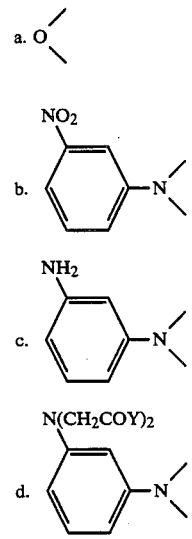

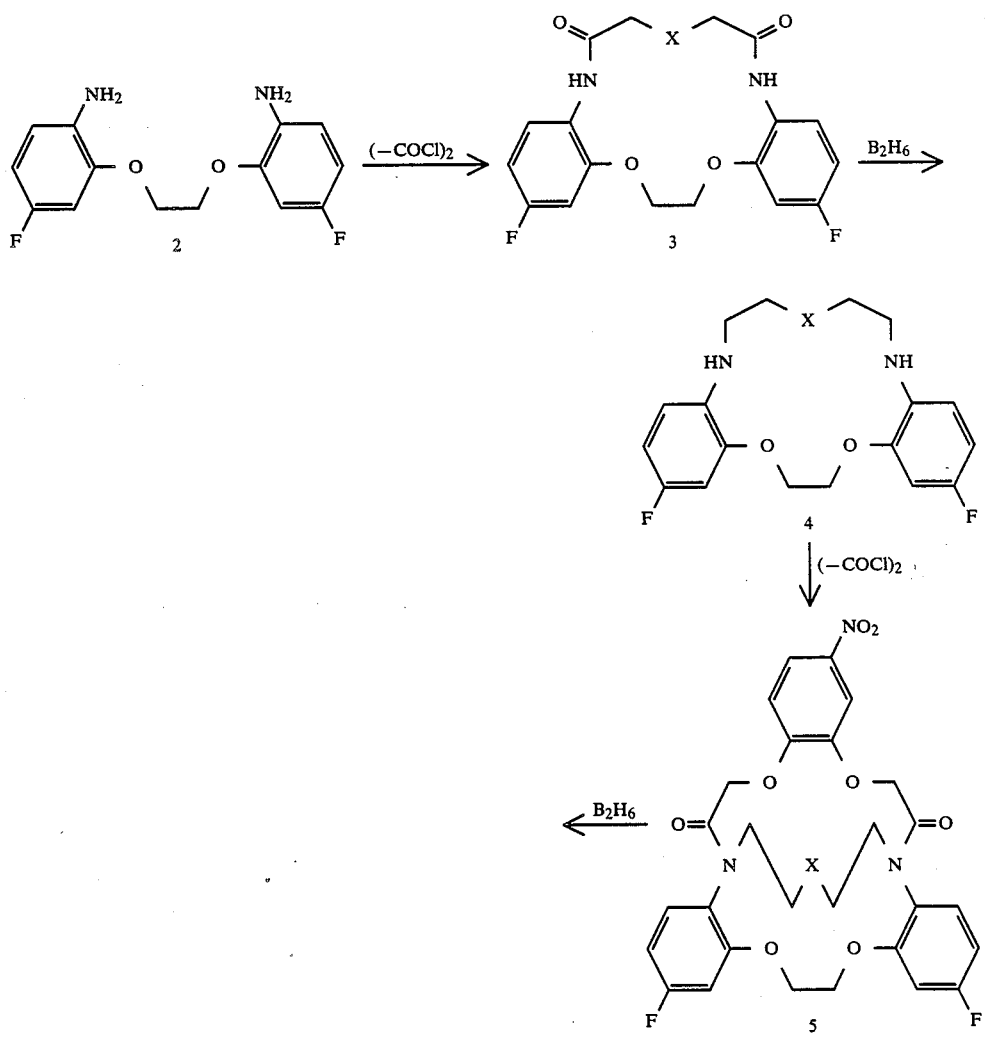

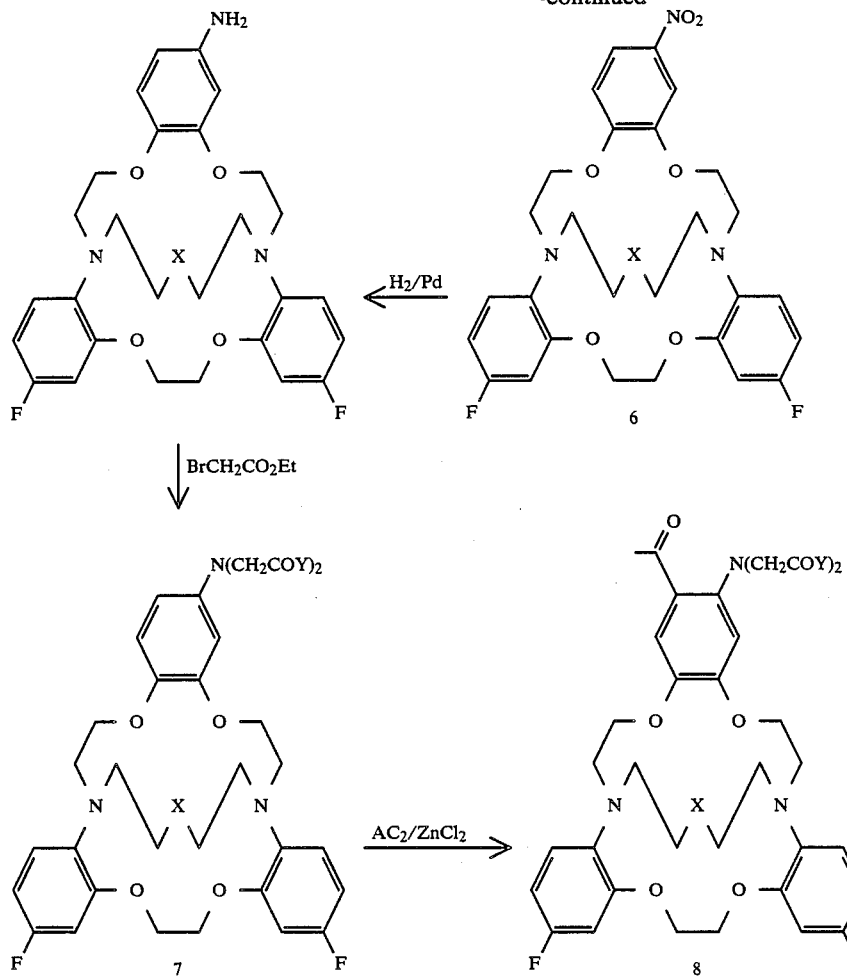

EXAMPLE 1

3,2-8,9-Bis [1-fluoro-3,4 benzo]-1,10-diaza-4,7,13-trioxa-cyclopentadecane-11, 15-dione (3a)

1,2-Bis (2-amino-5-fluorophenoxy) ethane (2) and pyridine (1.5 ml) were dissolved in methylene chloride (dry and ethanol free, 250 ml). A similar solution of an equimolar amount of diglycoloyl chloride (1.7 g) was prepared. The two solutions were added concurrently dropwise over one hour to, well stirred, boiling methylene chloride under reflux, protected from moisture. After a short further period of heating the solvent was removed in vacuo. The froth obtained was triturated with methanol and filtered to remove the polymeric side products and the product crystallised on additon of water (1 vol) (1.5 g, 40%) m.p. 237°–238° C. M+1 379 (FAB, glycerol).

3,2 -8,9-Bis [1-fluoro-3,4-benzo]-1,10-diaza-4,7,13-trioxa-cyclopentadecane (4a)

The cyclic amide 3a (1 g) in 1M borane in tetrahydrofuran (25 ml) was heated under reflux overnight and excess water added dropwise at reflux. After gas evolution had ceased the mixture was evaporated to dryness, dissolved in 80% ethanol and passed through a column of Dowex 2 X -8 hydroxyl form. Concentration in vacuo gave the crystalline product which was recovered by filtration, washed with water and dried (0.85 g, 92%) m.p. 136°–7° C.

3,2-8,9-Bis [1-fluoro-3,4-benzo]-13-[3-nitrophenyl]-4,7,-dioxa - 1,10,13-triazacyclopentadecane-11,15-dione (3b)

The acid chloride prepared from 3-nitroaniline diacetic acid (8.8 g) was dissolved in dichloromethane (dry and ethanol free, 900 ml). The diamine (2,9.7 g) and pyridine (10 ml) were dissolved in the same volume of dichloromethane. The two solutions were added simultaneously over two hours to well stirred dichloromethane (ca 500 ml to start) under reflux. The resulting solution was washed with dilute hydrochloric acid (2×) then with 1M potassium bicarbonate and dried over magnesium sulphate. The magnesium sulphate and some polymer were removed by filtration through a pad of hyflo supercell. The mixture was absorbed onto a pad of silica gel (500 ml) in a large sintered funnel and the product eluted with 50% ethylacetate, chloroform and recovered by evaporation in vacuo. The product was recrystallised by dissolution in a mixture of dichloromethane (2000 ml) and ethanol (500 ml) and evaporation to 700 ml. After cooling the product was recovered by filtration and washed with ethanol and dried to give a yellow solid (6.9 g 40%) m.p. 273° C., M+1 (FAB, glycerol).

3,2-8,9-Bis [1-fluoro-3,4-benzo]-13-[3-nitrophenyl]-4,7-dioxa -1,10,13-triaza cyclopentadecane (4b)

The diamide (3b) 1.0 g in 0.5M borane in THF (80 ml) was heated under reflux for two hours, water was added slowly at reflux to complete reaction and destroy the excess borane. The reaction mixture was partitioned between molar sodium carbonate and methylene chloride and the organic phase collected and evaporated to dryness. The crude gummy product was dissolved in concentrated hydrochloric acid (15 ml) and poured into a well stirred solution of sodium hydroxide (10 g) in water (200 ml) cooled in ice. The yellow product was collected by filtration, washed with water and dried (0.9 g 96%) m.p. 85°–90°.

3,2-8,9-Bis [1-fluoro-3,4-benzo]-14,15-[4-nitro-1,2-benzo]-1,10-diaza-4,7,13,16,21-pentaoxabicyclo[8,8,5]tricosane-11,18-dione (5a)

The diamine (4a, 2.0 g) and pyridine (2 ml) were dissolved in the minimum volume of dichloromethane (dry and ethanol free). An equimolar quantity of 4-nitro catechol-O,O-diacetyl chloride (1.76 g) was dissolved in an equal volume of dichloromethane. The two solutions were added concurrently over 2 hours to well stirred dichoromethane under reflux. The reaction mixture was evaporated to dryness in vacuo, dissolved in dichloromethane, some hyflo supercell added and the bulk of the polymer side product precipitated onto the hyflo by addition of an equal volume of methanol, and removed by filtration. Evaporation gives an oil which was purified by silical gel chromatography in 5% methanol in methylene chloride. Evaporation in vacuo gave a solid which was collected by filtration from methanol (0.95 g 30%) m.p. 264°–6° C.; M+23, 608 (FAB, glycerol), n.m.r. (CDCl$_3$, 60 MHz δ3.4 (m, 8H), 4.3 (m, 8H), 6.8–8 (m, 9H).

3,2-8,9-Bis [1-fluoro-3,4-benzo]-14,15-[4-nitro-1,2-benzo]-1,10-diaza -4,7,13,16,21-pentaoxabicyclo [8,8,5] tricosane (6a)

The diamide (5a, 500 mg) was heated under reflux for two days in 1M borane in tetrahydrofuran and the reaction completed by the slow addition of water at reflux. The reaction mixture was evaporated to low volume, the precipitate dissolved by the addition of 6N hydrochloric acid and the evaporation continued to remove the remaining organic solvents. The product was dissolved by the addition of hydrochloric acid, precipitated with concentrated ammonia and recovered by filtration. TLC performed on ammonium chloride impregnated silica plate in 10% methanol chloroform. The product was purified by column chromatography on silica (50 g) impregnated with ammonium chloride (5 g) eluating with 10% methanol in dichloromethane. Evaporation gave a solid (410 mg, 78%) m.p. 164°–5° C.

3,2-8,9-Bis [1-fluoro-3,4-benzo]-14,15-[4-di(ethoxycarbonylmethyl) amino-1,2-benzo]-1,10-diaza-4,7,13,16,21-pentaoxabicyclo[8,8,5] tricosane (7a i)

The nitro diamine (6a, 400 mg) was hydrogenated in ethanol (100 ml) and toluene (100 ml) over 10% Pd/C (100 mg) until hydrogen uptake ceased (48 ml, 2 days). The solvent was removed in vacuo and the product dried over phosphorous pentoxide. The solid (with catalyst) was added to a mixture of ethyl bromoacetate (2 g), proton sponge (2 g) and a few crystals of potassium iodide in acetonitrile (5 ml) and heated under nitrogen, under reflux for two days. The cooled solution was diluted with toluene, filtered and the filtrate washed with ammonium phosphate solution (1M, pH 4.0 3×), then water and evaporated to dryness and crystallised from ether/petroleum ether to give the product (200 mg, 40%) m.p. 168°–70° C., M+23, 722, (FAB glycerol): n.m.r. (CDCl$_3$ 60 MHz) δ 1.2 (t, 8 Hz, 6H), 3.15 (t,6 Hz, 4H) 3.45 (t, 6 Hz 4H) 3.9 (m, 8H) 4.0 (S, 4H) 4.05 (S, 4H), 4.1 (q,8 Hz,4H), 6.0–7.2 (m, 9H). The free acid (7a ii) was prepared by hydrolysis for 2 hours at 50° C. in ethanol solution with tetramethyl ammonium, or potassium, hydroxide in 50% excess, added as a molar solution in water, neutralised with dil hydrochloric acid and evaporated to dryness. The sodium content was minimised by prewashing all equipment used with potassium chloride solution and milliQ purified water.

3,2-8,9-Bis [1-fluoro-3,4-benzo]-14,15 -[4-nitro-1,2-benzo]-21-[3-nitrophenyl]-4,7,13,16-tetraoxa-1,10,21-triazabicyclo [8,8,5] tricosane-11,18-dione (5b)

The amine (4b, 4.7 g) was dissolved in the minimum volume of dichloromethane (2 ml) and added concurrently with a solution of 4-nitro catechol-OO-diacetoyl chloride (3.1 g) in the same volume of dichloromethane to well stirred dichloromethane under reflux. When the addition was complete (2 hours) the solution was washed with dilute hydrochloric acid (0.1M) then with potassium bicarbonate solution and dried over magnesium sulphate. The product was absorbed onto silica gel (500 g) and eluted with 25% ethyl acetate in chloroform. The product was isolated by evaporation, in vacuo, to low volume and filtration from ethyl acetate to give a yellow powder (3.1 g, 44%) m.p 195°–205° C., M+1 706 (FAB glycerol).

3,2-8,9-Bis [1-fluoro-3,4-benzo]-14,15 -[4-nitro-1,2-benzo]-21-[3-nitrophenyl]-4,7,13,16-tetraoxa-1,10,21-triazabicyclo [8,8,5] tricosane (6b)

The diamide (5b, 3.0 g) was heated with 1M borane in THF (80 ml) overnight, water was added at reflux, with care, to complete the reaction and destroy the excess reagent. The solvent was removed in vacuo and water added to dissolve the boric acid and the product was collected by filtration, washed with water and dried (2.8 g, 97%) M+23 700 (FAB glycerol), M+1 678 (FAB glycerol +H$_3$PO$_4$), a sample further purified by silica gel chromatography in 2% ether in dichloromethane, and crystallised from methanol m.p 226°–7° C.

3,2-8,9-Bis [1-fluoro-3,4-benzo]-14,15 -[4-amino-1,2-benzo]-21-[3-aminophenyl]-4,7,13,16-tetraoxa-1,10,21-triazabicyclo [8,8,5] tricosane (6c)

The dinitro compound (6b) was hydrogenated over 10% Pd/C in 50% toluene: ethanol for three days to complete uptake of hydrogen and evaporated to dryness.

3,2-8,9-Bis [1-fluoro-3,4-benzo]-14,15-[4-di(ethoxycarbonylmethyl) amino-1,2-benzo]-21-[3-di(ethoxycarbonylmethyl-)amino phenyl]-4,7,13,16-tetraoxa-1,10,21-triazabicyclo [8,8,5] tricosane (7d i)

The amine (6c, 450 mg), sodium iodine (anhydrous 1.1 g), ethyl bromoacetate (0.45 ml) and proton sponge (720 mg) in acetonitrile (5 ml) heated under nitrogen, under reflux, for 24 hrs. The cooled mixture was diluted with toluene, filtered and washed with ammonium phosphate (1M, pH4,3×) water and then dried with potassium carbonate, chromatography over silica in 50% dichloromethane:ether and preparative thin layer chromatography in 10% methanol in chloroform gave the product as a froth from dichloromethane (390 mg, 59%) M+23, 984 (FAB glycerol). n.m.r. (CDCl$_3$ 60 MH$_z$) 1.18 (t, 8 Hz, 6H), 1,21 (t, 8 Hz 6H), 3.2 (broad t, 6 Hz, 4H), 3.6 (broad s,4H) 3.8 (broad t, 6 Hz, 4H), 4.0 (s, 4H) 4.05 (s, 4H) 4.1 (s, 8H) 4.10 (q, 8 Hz, 4H) 4.15 (q, 8 Hz, 4H) 5.8-7.3 (m, 13H).

The 400 MHz spectrum in DMSO was essentially the same as for 8d i, except for: a double doublet at δ 6.2 (2.5 , 8 Hz); a doublet at δ 7.02 (8 Hz) in place of the singlet; and a doublet at δ 6.4 (2.5 Hz) in place of the singlet at δ 7.2; and no acetyl singlet δ at 2.7.

The free acid (7 d ii) was prepared by hydrolysis with a two fold excess of potassium hydroxide in 50% aqueous ethanol at 50° C. for two hours under N$_2$. The ethanol was removed in vacuo and the product precipitated at pH 3.0 with hydrochloric acid, filtered, washed with water and dried.

3,2-8,9-Bis [1-fluoro-3,4-benzo]-14,15-[1 -di(ethoxycarbonylmethyl)amino-2-acetyl-4,5-benzo]- 21-[3-di(ethoxycarbonylmethyl)aminophenyl]- 4,7,13,16-tetraoxa-1,10,21-triazabicyclo [8,8,5] tricosane (8d i)

The cryptand (7d i) (150 mg) and zinc chloride (ACS, 100 mg) were heated under reflux in acetic anhydride (10 ml) for thirty mins. The solvent was removed in vacuo and the residue stirred with potassium bicarbonate solution (1M) for 30 mins. The suspension was extracted with dichloromethane. The separated organic phase after evaporation was purified by preparative thin layer chromatography on silica in 7.5% methanol in chloroform, to give the product as a froth (80 mg, 52%), M+23 1026 (FAB glycerol) n.m.r. 400 MHz, DMSO 1.09 (t, 7 Hz, 6H), 1.18 (t, 7 Hz, 6H), 2.70 (S, 3H), 3.26 (m, 4H) 3.50 (m, 4H), 3.92 (m, 4H), 4.06 (S, 2H) 4.09 (m, 2H), 4.14 (S, 4H), 4.17 (q, 7 Hz 4H) 4.29 (q, 7 Hz, 4H) 4.37 (S, 4H) 4.48 (m, 4H) 6.05 (d (b), 7.8 Hz, 1H) 6.07 (S (b), 1H), 6.42 (d(b), 7.8 Hz, 1H), 7.02 (S, 1H), 7.07 (m, 2.7, 11, 8.9 Hz, 2H) 7.16 (S, 1H), 7.31 (t, 7.8 Hz, 1H) 7.31 (d,d, 11,2.7 Hz, 1H) 7.35 (d,d,11,2.7 Hz, 1H) 7.47 (d,d,8.9, 6.3 Hz, 1H), 7.63 (d, d, 8.9, 6.3 Hz, 1H).

The free acid (8d ii) was prepared as for (7d ii).

Other compounds according to the invention can readily be made by modifications of the above reaction sequence that are well within the skill of the art. Example 2 illustrates this point.

EXAMPLE 2

2,3-9,8-Bis [1-fluoro-3,4-benzo]-14,15-[4-nitro-1,2-benzo]-1,10-diaza-4,7,13,16-tetraoxacyclooctadecane-11,18-dione (A)

1,2-Bis (2-amino-4-fluorophenoxy)ethane (32.8 g), pyridine (20 ml) in dichloromethane (1L) and a solution of the acid chloride made from 4-nitro-O,O-diacetic acid (31.75 g) in dichloromethane (1L) were added simultaneously to well stirred dichloromethane (1L) over 2 hours and left overnight. The resulting solution was stirred with hydrochloric acid (2M, 500 ml), filtered through hyflo supercell, separated and dried with sodium carbonate. The product was absorbed onto a column of silica gel (500 g). On attempted elution with 1% ethyl acetate in chloroform the product crystallised on the column. The column was extruded, the top portion discarded and the remainder extracted by boiling with 2% ethyl acetate in chloroform (3×2L). Evaporation and filtration from ethyl acetate gave the title compound (44.8 g, 74%) m.p. 265°-6°C., M+1, 516 (FAB, NOBA.)

2,3-9,8-Bis[1-fluoro-3,4-benzo]-14,15 [4-nitro-1,2-benzo]-1,10-diaza-4,7,13,16 tetraoxacyclooctadecane (B)

The diamide A (40 g) was dissolved in borane, tetrahydrofuran (1M, 500 ml) at reflux and a solution of water (12 ml) in tetrahydrofuran (100 ml) added dropwise over 1 hour. The solution was then treated with hydrochloric acid (conc. 50 ml) and poured with good stirring into excess sodium hydroxide solution (1M) and petroleum ether (40–60) and the product collected by filtration and dried (35.5 g 95%) m.p. 243°-4° C., M+477 (FD).

2,3-9,8-Bis[1-fluoro-3,4-benzo]-14,15-[4-nitro-1,2-benzo]-21-[3-nitro-1-naphthyl]-4,7,13,16-tetraoxa-1,10,21-triazabicyclo [8,8,5]tricosane-19,23-dione (C)

The diaza crown ether B, (10.8 g) was prepared in a finely divided state by dissolution in boiling ethanol (100 ml) with the addition of hydrochloric acid (conc. 50 ml) and the hot solution was poured into well stirred ammonia (d.880, 1 L). The fine suspension was collected by filtration and dried in vacuo at 80° C. overnight and finally over phosphorus pentoxide at 150° C. in vacuo for five hours. The dry solid was suspended in dichloromethane (1.5 L) and stirred well. 3-nitro-1-naphthylamine-N-diacetyl chloride (10% excess, 8.3 g) in dichloromethane (1 L) was added over 4 hours whilst a solution of pyridine (3.4 g) in dichloromethane was added concurrently but with a 30 minute delay. When additions were complete, after 4.5 hours, a further 4 g of pyridine was added and the mixture left for 1 hour.

The resulting solution was washed with dilute hydrochloric acid (2M, 500 ml), dried with sodium carbonate, filtered through hyflo supercell and absorbed onto a column of silica (200 g). Any traces of diamine remaining were eluted with dichloromethane (1 L). The product was eluted as a coloured band with chloroform (about 1 L), seeded and left to crystallise overnight, and then collected by filtration (12.5 g, 75%), decomposition at about 200° C., non-melting at <330° C., M+1, 756 (FAB, NOBA).

2,3-9,8-Bis[1-fluoro-3,4-benzo]-14,15-[4-nitro-1,2-benzo]-21-[3-nitro-1-naphthyl]-4,7,13,16-tetraoxa-1,10,21-triazabicyclo][8,8,5] tricosane (D).

The diamide C (12.5 g) was dissolved in borane, tetrahydrofuran (1M, 600 ml) under reflux and wate (5.4 ml) in tetrahydrofuran (150 ml) was added dropwise over 1 hour. Further water (25 ml) was added after 45 mins. The solution was evaporated to dryness in vacuo and triturated with water (500 ml). The product was collected by filtration, washed with water and dried (10.2 g, 85%), sinters at about 150° C., decomposition at about 200° C., M+1, 728 (FAB, NOBA).

2,3-9,8-Bis[1-fluoro-3,4-benzo]-14,15-[4-amino-1,2-benzo]-21-[3-amino-1-naphthyl]-4,7,13,16-tetraoxa-1,10,21-triazabicyclo 8,8,5] tricosane (E)

The dinitro cryptand D, (10.2 g) in tetrahydrofuran (200 ml) was treated with stannous chloride dihydrate (50 g) in hydrochloric acid (conc, 100 ml) for two hours. The solution was poured into a solution of potassium hydroxide (500 g) in water (1 L) and extracted with dichloromethane until all visible solids were dissolved. The combined extracts were washed with potassium hydroxide solution (5M), dried with magnesium sulphate and evaporated with toluene (ca 50 ml). The product was allowed to crystallise at 0° C. and collected by filtration (7.3 g, 79%) m.p. 155°-160° M+1 668 (FAB, NOBA). All solutions were kept deoxygenated with nitrogen bubbling.

2,3-9,8-Bis [1-fluoro-3,4-benzo]-14,15[4-di(ethoxycarbonylmethyl)amino-1,2-benzo]-21-[3-di(ethoxycarbonylmethyl)amino-1-naphthyl]-4,7,13,16-tetraoxa-1,10,21-triazabicyclo-[8,8,5] tricosane (F).

The amine E (7.3 g), proton sponge (15 g), ethyl bromoacetate (15 g), sodium iodide (15 g) and acetonitrile (50 ml) were heated under $N_2$, under reflux for 24 hrs. The reaction mixture was diluted with toluene and ammonium phosphate solution (1M, pH 4),filtered through hyflo supercell and separated. The toluene phase was washed with more ammonium phosphate (3×) and potassium bicarbonate (1M), dried with magnesium sulphate and evaporated and purified by chromatography in ethyl acetate/toluene over silica gel (9 g, 78%), M+1, 1012 (FAB, NOBA).

2,3-9,8-Bis [1-fluoro-3,4-benzo]-14,15-[4-di(ethoxycarbonylmethyl)amino-5-acetyl-1,2-benzo]-21-[3-di(ethoxycarbonylmethyl)-amino-4-acetyl-1-naphthyl]-4,7,13,16-tetraoxa-1,10,21-triazabicyclo[8,8,5]tricosane (G).

An acylation reagent was prepared as follows. Zinc chloride (14 g) was dried by fusion over a bunsen flame. Sodium chloride (6 g) was added to the melt and mixed well over gentle heat to give a clear solution. On cooling the solid was dissolved in acetic anhydride (140 ml).

The cryptand ethyl ester F (1.5 g) was dissolved in the acylation reagent (30 ml) and stirred in an oil bath at 100° C. for 30 mins. Acetic anhydride (10 ml) was then added and removed by vacuum distillation over a period of 1 hour, to remove side-product acetic acid, and the reaction mixture heated for a further 1 hour. The yellow solution was then cooled and poured onto a mixture of water and toluene with potassium bicarbonate (50 g) and stirred well for 1 hour. After filtration with hyflo supercell, the phases were separated and the organic phase washed with potassium chloride solution, dried with magnesium sulphate and evaporated, (t.l.c, activated silica, 30% ethyl acetate in toluene and 5% isopropanol in dichloromethane).

The oil was chromatographed on dry silica (100 g) in 15% ethyl acetate in toluene, the first eluted band was collected, ensuring that the slower running impurity was not included as this distorts the second chromatography. The product was re-chromatographed on dry silica (150 g), pre-equilibrated with 3% isopropanol in dichloromethane (2 L), eluting with the same solvent to give the pure product as a dry froth (0.7 g, 43%), n.m.r. (CDCl$_3$, 400 MHz) δ 1.139 (t 7.1 Hz, 6H), 1.173 (t,7.0 Hz, 6H), 2.685 (S, 3H), 2.690 (S, 3H), 2.941 (m, 2H), 3.21 (m, 2H), 3.44 (m,2H), 3.64 (m, 2H), 3.65(m, 2H), 3.91 (m, 4H), 4.07 (m, 4H) 3.950 (S, 4H), 3.956 (q,7.1 Hz, 4H), 3.970 (S, 4H), 4.055(q, 7.0 Hz, 2H), 4.060(q, 7.0Hz, 2H) 4.45 (m, 2H), 6.630(d,t,3,9 Hz, 1H), 6.636 (S, 1H), 6.653(d,t,3, 9Hz,1H), 6.760(d,d,3,10Hz, 1H), 6.785(d,d,3,10 Hz, 1H), 6.872(d,d,5,9Hz, 1H), 6.881 (d,d,5,9 Hz,1H), 6.912 (S,1H), 7.316(d, d, d, 1.5, 7.0, 8.5 Hz, 1H), 7.364 (d,d,d, 1.5, 7.0, 8.5 Hz, 1H), 7.504 (S, 1H), 7.642 (d,d,1.5, 8.5 Hz, 1H), 8.246 (d,d, 1.5, 8.5, Hz, 1H), M+1, 1096 (FAB, NOBA).

EXAMPLE 3

The tetra-acetoxymethyl ester of the free acid (8d ii) of Example 1 was prepared in the following manner:

(a) Hydrolysis—The ethyl ester (10 mg) in ethanol (2 ml) was treated with tetrabutyl ammonium hydroxide solution in water (1.6M, 50 μL) (8 molar equivalents), degassed with nitrogen and heated at 60° C. for 2 hours. The solvent was evaporated in vacuo and the residue dissolved in water, degassed with nitrogen and the heating continued at 60° C. for 2 hours. The water was then evaporated and the residue dried.

(b) Esterification—The residue was dissolved in dichloromethane, treated with excess acetoxymethyl bromide overnight, evaporated to dryness, triturated with 75% ethyl acetate in toluene, filtered to remove salts and flash chromatographed on silica gel. The product was finally purified by high performance liquid chromatography on a silica support using a dichloromethane-isopropanol gradient.

This ester satisfies the criteria set out above for use as a probe for intracellular sodium:

(i) It carries two fluorine atoms, which show a fluorine chemical shift on sodium binding.
(ii) The compound has a high selectivity for sodium over all other ions and in particular over potassium.
(iii) The sodium complex has a dissociation constant of 40 mM.
(iv) The compound carries four acetoxymethyl ester groups.
(v) The compound has not shown any adverse effect on cellular function.

To demonstrate these properties, the following experiment was performed.

EXAMPLE 4

Lymphocytes (1 ml packed cells) were prepared from pig mesenteric lymphnodes by standard procedure in RPM1 medium. The cells suspended in RPM1 (200 ml) were treated with the tetra-acetoxymethyl ester of Example 3 (4.5 mg) in DMSO (100 μl) and incubated at 37° C. for 1 hour. The cells were isolated by centrifugation and suspended in RPM1 (20 ml) in the spectrometer probe, with continuous dialysis against oxygenated medium and the data collected. The signal appeared after 3 hours and was collected for a further 3 hours.

The 19F chemical shift was compared to a standard, namely 1,2-bis (2-amino-5-fluorophenoxy) ethane-N,N,N',N'-tetracetic acid, and was found to be 5.99 ppm downfield from that of the standard, indicating a sodium ion concentration of about 13 mM.

EXAMPLE 5

Fluorescence titrations: Ionic titrations of chelator fluorescence were performed on a Perkin Elmer 44E spectrofluorometer at a chelator concentration of 10 μM in 100 mM tris/acetic acid buffer at 37° C. Fluorescence emission from all of the chelators was monitored at a constant wavelength between 370 and 390 nm. The excitation spectra from 210 to 350 nm were recorded in the ratio mode and the proportion of $M^{n+}$ chelator complex was calculated from the fluorescence intensities at the most sensitive excitation wavelengths. The binding constants were estimated graphically from plots of log (bound/free) chelator against log free $[M^{n+}]$. (Slopes were $1.00 \pm <0.05$).

NMR titrations: Nmr spectra were recorded on Bruker WH 200 or Am 400 spectrometers at 188 or 376 MHz respectively at chelator concentrations between 5 and 10 mM in the same buffer as for fluorescence titrations but containing 20% $D_2O$ at 37° C. The spectra were obtained with an acquisition time of 1.0 sec. and a 90° pulse and were processed with resolution enhancement (−0.5 of the observed line width) and appropriate gaussian sensitivity enhancement. The proportion of $M^{n+}$-chelator complex was calculated from the integrals of the resolved free and bound chelator $^{19}F$ resonances, or from the chemical shift of complexes in fast exchange. The apparent affinities were determined graphically as for the fluorescence data, but using a two step iteration from the affinity derived from the fluorescence data when the dissociation constant was close to the chelator concentration in the nmr titrations.

Results are set out in Tables 1 and 2.

TABLE 1

| Cation Binding Constants (log k) at 37° C. | | | |
|---|---|---|---|
| Compound | 7a | 7d | 8d |
| Na+ | 6[a] | 1.6[a,b] | 1.3[a]–1.6[b] |
| K+ | 2.3[a] | <−1[b] | <−1[b] |
| Mg2+ | <−1[b] | <−1[b] | <−1[b] |
| Ca2+ | <−1[b] | <−1[b] | <−1[b] |
| H+ | nd | 7.0[b] | 5.5[b],8.4[b] |

[a] from NMR,
[b] from fluorescence at 370 nm,
nd: not determined

TABLE 2

| Cation Induced Chemical Shifts (ppm downfield) | | | |
|---|---|---|---|
| Compound | 7a | 7d | 8d |
| Na+ | 3.09(s) | 1.96(f) | 2.00(f) |
| K+ | 1.09(f) | 0 | 0 |
| Mg2+ | 0 | 0 | 0 |
| Ca2+ | 0 | 0 | 0 |

TABLE 2-continued

| Cation Induced Chemical Shifts (ppm downfield) | | | |
|---|---|---|---|
| Compound | 7a | 7d | 8d |
| *H+ | nd | −0.5 | −0.25 | f = fast exchange,
s = slow exchange,
*ppm per unit of pH at pH 7.0.

I claim:

1. A compound having the property of selectively binding sodium ions in the presence of potassium ions and having the formula:

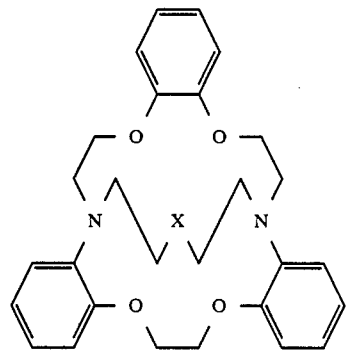

where X is:

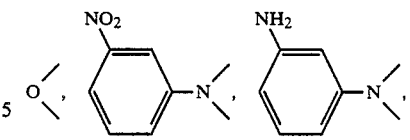

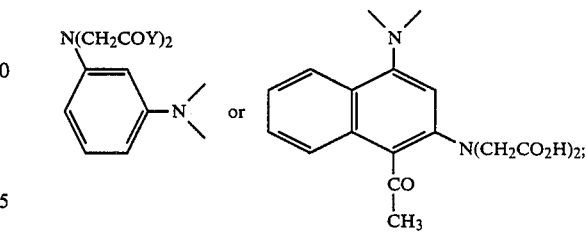

and Y is —OEt or —OH and where any or all of the aromatic rings may carry substituents at any free position and/or may form part of a fused aromatic ring system.

2. A compound as claimed in claim 1, wherein at least one aromatic ring is substituted by a spectroscopic reporter group.

3. A compound as claimed in claim 2, wherein at least one aromatic ring is substituted by a group which permits the compound to enter and remain in a cell.

4. A compound as claimed in claim 3, wherein the group is an acetoxymethyl ester of an anilinodiacetic acid.

5. A compound as claimed in claim 1, wherein at least one aromatic ring is substituted by an electron donating or withdrawing group.

* * * * *